United States Patent
Fryer et al.

(10) Patent No.: US 10,814,027 B2
(45) Date of Patent: Oct. 27, 2020

(54) STERILIZATION-ASSISTANCE DEVICE

(71) Applicant: ASP Global Manufacturing GmbH, Schaffhausen (CH)

(72) Inventors: Ben Fryer, Lake Forest, CA (US); Han Chin, Corona, CA (US); Behnam Amin, Mission Viejo, CA (US); Raya Majdanishabestari, Troy, MI (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 74 days.

(21) Appl. No.: 15/834,233

(22) Filed: Dec. 7, 2017

(65) Prior Publication Data

US 2019/0175775 A1 Jun. 13, 2019

(51) Int. Cl.
*A61L 2/24* (2006.01)
*A61L 2/28* (2006.01)
(Continued)

(52) U.S. Cl.
CPC ........ *A61L 2/24* (2013.01); *A61B 1/12* (2013.01); *A61B 1/123* (2013.01); *A61L 2/02* (2013.01); *A61L 2/20* (2013.01); *A61L 2/208* (2013.01); *A61L 2/28* (2013.01); *A61L 2202/14* (2013.01); *A61L 2202/24* (2013.01)

(58) Field of Classification Search
CPC ..... A61L 2/24; A61L 2/02; A61L 2/20; A61L 2/28; A61L 2/208; A61L 2202/24; A61L 2202/14; A61B 1/12; A61B 1/123
See application file for complete search history.

(56) References Cited

U.S. PATENT DOCUMENTS 3,701,434 A 10/1972 Moore
4,416,417 A 11/1983 Sanderson et al.
(Continued)

FOREIGN PATENT DOCUMENTS

AU 198820053 A 2/1989
AU 622412 B2 4/1992
(Continued)

OTHER PUBLICATIONS

Yuanyuan Xu et al.; "The Boom in 3D-Printed Sensor Technology"; Sensors 2017; vol. 17; pp. 1-37.
(Continued)

*Primary Examiner* — Regina M Yoo
(74) *Attorney, Agent, or Firm* — Etan S. Chatlynne; Roberts Calderon Safran & Cole P.C.

(57) ABSTRACT

A sterilization-assistance device is described herein. In some embodiments, the sterilization-assistance device comprises a dry booster and at least one measurement device attached to the dry booster. In various embodiments, the at least one measurement device may include a strain gauge. In various embodiments, the at least one measurement device may include a pressure sensor. In various embodiments, the at least one measurement device may include a pressure sensor and a strain gauge. The sterilization assistance device may also include a communication module. The communication module may be a wireless-communication module. The measurement device may provide indications that the dry booster has become detached from an endoscope during a sterilization procedure.

14 Claims, 1 Drawing Sheet

(51) Int. Cl.
*A61L 2/20* (2006.01)
*A61L 2/02* (2006.01)
*A61B 1/12* (2006.01)

(56) References Cited

U.S. PATENT DOCUMENTS

| | | |
|---|---|---|
| 4,637,378 A | 1/1987 | Sasa |
| 4,748,003 A | 5/1988 | Riley |
| 4,878,484 A | 11/1989 | Miyagi |
| 4,943,414 A | 7/1990 | Jacobs et al. |
| 5,084,239 A | 1/1992 | Moulton et al. |
| 5,165,503 A | 11/1992 | Hoffman |
| 5,279,317 A | 1/1994 | Bowman et al. |
| 5,288,467 A | 2/1994 | Biermaier |
| 5,308,406 A | 5/1994 | Wallock et al. |
| 5,320,119 A | 6/1994 | Griffiths |
| 5,348,711 A | 9/1994 | Johnson et al. |
| 5,413,758 A | 5/1995 | Caputo et al. |
| 5,471,706 A | 12/1995 | Waock et al. |
| 5,492,672 A | 2/1996 | Childers et al. |
| 5,511,568 A | 4/1996 | Bowman et al. |
| 5,533,518 A | 7/1996 | Vogler |
| 5,547,456 A | 8/1996 | Strobl et al. |
| 5,551,462 A | 9/1996 | Biermaier |
| 5,556,607 A | 9/1996 | Childers et al. |
| 5,580,530 A | 12/1996 | Kowatsch et al. |
| 5,634,880 A | 6/1997 | Feldman et al. |
| 5,645,796 A | 7/1997 | Caputo et al. |
| 5,667,495 A | 9/1997 | Bitdinger et al. |
| 5,733,503 A | 3/1998 | Kowatsch et al. |
| 5,807,238 A | 9/1998 | Feldman et al. |
| 5,868,667 A | 2/1999 | Lin et al. |
| 5,906,802 A | 5/1999 | Langford |
| 5,961,921 A | 10/1999 | Addy et al. |
| 5,961,937 A | 10/1999 | Gobbato |
| 5,980,825 A | 11/1999 | Addy et al. |
| 6,030,579 A | 2/2000 | Addy et al. |
| 6,068,817 A | 5/2000 | Addy et al. |
| 6,083,458 A | 7/2000 | Lin et al. |
| 6,099,812 A | 8/2000 | Allen et al. |
| 6,132,680 A | 10/2000 | Addy et al. |
| 6,162,395 A | 12/2000 | Kowanko |
| 6,174,502 B1 | 1/2001 | Addy et al. |
| 6,187,265 B1 | 2/2001 | Wu et al. |
| 6,193,932 B1 | 2/2001 | Wu et al. |
| 6,264,902 B1 | 7/2001 | Howlett |
| 6,312,646 B2 | 11/2001 | Kowanko |
| 6,319,480 B1 | 11/2001 | Addy et al. |
| 6,325,972 B1 | 12/2001 | Jacobs et al. |
| 6,365,103 B1 | 4/2002 | Fournier |
| 6,379,631 B1 | 4/2002 | Wu |
| 6,451,255 B1 | 9/2002 | Williams et al. |
| 6,495,100 B1 | 12/2002 | Lin et al. |
| 6,528,017 B2 | 3/2003 | Jacobs et al. |
| 6,534,002 B1 | 3/2003 | Lin et al. |
| 6,569,128 B1 | 5/2003 | Christensen et al. |
| 6,572,819 B1 | 6/2003 | Wu et al. |
| 6,589,481 B1 | 7/2003 | Lin et al. |
| 6,627,150 B1 | 9/2003 | Wang et al. |
| 6,656,426 B1 | 12/2003 | Wang et al. |
| 6,692,693 B2 | 2/2004 | Wu |
| 6,977,061 B2 | 12/2005 | Lin et al. |
| 7,132,089 B2 | 11/2006 | Lacabanne |
| 7,179,419 B2 | 2/2007 | Lin et al. |
| 7,229,591 B2 | 6/2007 | Wu et al. |
| 7,252,800 B2 | 8/2007 | Jacobs et al. |
| 7,285,254 B2 | 10/2007 | Lin et al. |
| 7,294,305 B2 | 11/2007 | Lin et al. |
| 7,300,638 B2 | 11/2007 | Williams et al. |
| 7,468,159 B2 | 12/2008 | Lin et al. |
| 7,569,180 B2 | 8/2009 | Kohler et al. |
| 7,670,550 B2 | 3/2010 | Lin et al. |
| 7,803,316 B2 | 9/2010 | Lin et al. |
| 7,862,769 B2 | 1/2011 | Kaiser |
| 7,993,602 B2 | 8/2011 | Moriyama et al. |
| 8,118,042 B2 | 2/2012 | Ngo et al. |
| 8,298,494 B2 | 10/2012 | Komiya et al. |
| 8,444,930 B2 | 5/2013 | Komiya et al. |
| 8,444,940 B2 | 5/2013 | Komiya et al. |
| 8,460,176 B2 | 6/2013 | McGrath |
| 8,658,092 B2 | 2/2014 | Kohler et al. |
| 8,840,836 B2 | 9/2014 | Olson |
| 8,926,501 B2 | 1/2015 | Powell et al. |
| 9,060,804 B2 | 6/2015 | Meyer |
| 9,132,456 B2 | 9/2015 | Kawai et al. |
| 9,144,469 B1 | 9/2015 | Geddis et al. |
| 9,216,074 B2 | 12/2015 | Vedovelli |
| 9,295,374 B2 | 3/2016 | Metras |
| 9,533,136 B2 | 1/2017 | Midgette et al. |
| 9,922,533 B2 | 3/2018 | Hayes et al. |
| 2001/0000227 A1 | 4/2001 | Kowanko |
| 2001/0036422 A1 | 11/2001 | Lin et al. |
| 2002/0015673 A1 | 2/2002 | Moriyama |
| 2002/0191938 A1 | 12/2002 | Sheetz et al. |
| 2003/0026729 A1 | 2/2003 | Wu et al. |
| 2004/0105780 A1 | 6/2004 | Lin et al. |
| 2004/0118440 A1 | 6/2004 | Sasaki et al. |
| 2005/0000553 A1 | 1/2005 | Noguchi et al. |
| 2005/0191208 A1 | 9/2005 | Lin et al. |
| 2005/0191209 A1 | 9/2005 | Lin et al. |
| 2005/0191222 A1 | 9/2005 | Lin et al. |
| 2005/0216029 A1 | 9/2005 | Gingrich et al. |
| 2005/0260097 A1 | 11/2005 | Williams et al. |
| 2006/0263245 A1 | 11/2006 | Watanabe et al. |
| 2007/0258873 A1 | 11/2007 | Wu et al. |
| 2008/0131342 A1 | 6/2008 | Wu et al. |
| 2009/0107529 A1 | 4/2009 | Lin et al. |
| 2009/0225517 A1 | 9/2009 | Nelson et al. |
| 2009/0324445 A1 | 12/2009 | Kohler et al. |
| 2012/0031506 A1 | 2/2012 | Komiya et al. |
| 2012/0275954 A1 | 11/2012 | Olson |
| 2013/0000746 A1 | 1/2013 | Komiya et al. |
| 2013/0098400 A1 | 4/2013 | Nguyen et al. |
| 2013/0156640 A1 | 6/2013 | Kohler et al. |
| 2015/0073214 A1 | 3/2015 | Ueda |
| 2015/0359599 A1 | 12/2015 | Fagan et al. |
| 2015/0374868 A1 | 12/2015 | Bruce et al. |
| 2017/0007731 A1* | 1/2017 | Sharma .............. A61L 2/07 |
| 2017/0210504 A1 | 7/2017 | Aguirre |
| 2017/0224434 A1 | 8/2017 | Schwatzbauer et al. |
| 2017/0224859 A1 | 8/2017 | Broninx et al. |
| 2019/0046024 A1 | 2/2019 | Morrison |
| 2019/0184048 A1 | 6/2019 | Fryer |
| 2019/0201568 A1 | 7/2019 | Rhodes |
| 2019/0388672 A1 | 12/2019 | McNeal et al. |

FOREIGN PATENT DOCUMENTS

| | | |
|---|---|---|
| AU | 4673796 A | 1/1997 |
| AU | 1744097 A | 7/1997 |
| AU | 1770197 A | 10/1997 |
| AU | 2454997 A | 10/1997 |
| AU | 700172 B2 | 12/1998 |
| AU | 9710398 A | 7/1999 |
| AU | 720169 B2 | 5/2000 |
| AU | 721001 B2 | 6/2000 |
| AU | 6556399 A | 7/2000 |
| AU | 723034 B2 | 8/2000 |
| AU | 733363 B2 | 5/2001 |
| AU | 7241900 A | 6/2001 |
| AU | 200072377 A1 | 6/2001 |
| AU | 3352301 A | 8/2001 |
| AU | 200118028 A | 6/2002 |
| AU | 755860 B2 | 1/2003 |
| AU | 755983 B2 | 1/2003 |
| AU | 766746 B2 | 10/2003 |
| AU | 769624 B2 | 1/2004 |
| AU | 771288 B2 | 3/2004 |
| AU | 755983 C | 7/2004 |
| AU | 2001233523 A | 9/2004 |
| AU | 2005249347 B2 | 12/2005 |
| AU | 2005227377 A1 | 4/2006 |
| AU | 2005227377 B2 | 6/2010 |
| BR | 8803795 A | 2/1989 |

(56) References Cited

FOREIGN PATENT DOCUMENTS

| | | |
|---|---|---|
| BR | 9602186 A | 4/1998 |
| BR | 9708498 A | 8/1999 |
| BR | 9805358 A | 11/1999 |
| BR | PI0504322 A | 6/2006 |
| BR | 9602186 B1 | 2/2010 |
| CA | 1321702 C | 8/1993 |
| CA | 2256040 A1 | 6/1999 |
| CA | 2050368 C | 3/2000 |
| CA | 2293199 A1 | 6/2000 |
| CA | 2357838 A1 | 7/2000 |
| CA | 2357843 A1 | 7/2000 |
| CA | 2329208 A1 | 6/2001 |
| CA | 2329385 A1 | 6/2001 |
| CA | 2298165 A1 | 8/2001 |
| CA | 2251153 C | 6/2005 |
| CA | 2241318 C | 9/2005 |
| CA | 2201572 C | 11/2005 |
| CA | 2566580 A1 | 12/2005 |
| CA | 2522509 A1 | 4/2006 |
| CA | 2298165 C | 5/2006 |
| CA | 2175867 C | 8/2006 |
| CA | 2221149 C | 10/2006 |
| CA | 2293199 C | 10/2006 |
| CA | 2329208 C | 12/2006 |
| CA | 2329385 C | 4/2007 |
| CA | 2357843 C | 4/2007 |
| CA | 2256040 C | 2/2008 |
| CA | 2566580 C | 2/2010 |
| CA | 2357838 C | 6/2010 |
| CA | 2522509 C | 5/2014 |
| CH | 688083 A5 | 5/1997 |
| CN | 1169877 A | 1/1998 |
| CN | 1223148 A | 7/1999 |
| CN | 1112938 C | 7/2003 |
| CN | 1765420 A | 5/2006 |
| CN | 1997407 A | 7/2007 |
| CN | 100371025 C | 2/2008 |
| CN | 101121025 A | 2/2008 |
| CN | 100496616 C | 6/2009 |
| CN | 1997407 B | 11/2010 |
| CN | 101121025 B | 1/2012 |
| CN | 102481092 A | 5/2012 |
| CN | 102871640 A | 1/2013 |
| CN | 102481092 B | 4/2014 |
| DE | 3819257 C1 | 7/1989 |
| DE | 3874837 T2 | 4/1993 |
| DE | 4404460 C1 | 6/1995 |
| DE | 69120174 T2 | 11/1996 |
| DE | 19858391 A1 | 7/1999 |
| DE | 69605548 T2 | 7/2000 |
| DE | 69626697 T2 | 1/2004 |
| DE | 69724958 T2 | 7/2004 |
| DE | 69726329 T2 | 11/2004 |
| DE | 69631561 T2 | 12/2004 |
| DE | 60019538 T2 | 5/2005 |
| DE | 69923758 T2 | 4/2006 |
| DE | 69635595 T2 | 8/2006 |
| DE | 69931280 T2 | 5/2007 |
| DE | 69933137 T2 | 8/2007 |
| DE | 69839085 T2 | 1/2009 |
| DE | 69931280 T3 | 1/2010 |
| DE | 19858391 B4 | 9/2012 |
| DK | 0799621 T3 | 3/2004 |
| EP | 0 212 426 B1 | 3/1987 |
| EP | 0302419 A2 | 2/1989 |
| EP | 345713 A2 | 12/1989 |
| EP | 0302419 A3 | 5/1990 |
| EP | 0345713 A3 | 7/1991 |
| EP | 0474137 A2 | 3/1992 |
| EP | 0474137 A3 | 8/1992 |
| EP | 0302419 B1 | 9/1992 |
| EP | 583465 A1 | 2/1994 |
| EP | 0345713 B1 | 9/1994 |
| EP | 0474137 B1 | 6/1996 |
| EP | 0742017 A2 | 11/1996 |
| EP | 0799621 A1 | 10/1997 |
| EP | 0742017 A3 | 1/1998 |
| EP | 0833704 A1 | 4/1998 |
| EP | 0907381 A1 | 4/1999 |
| EP | 0923949 A2 | 6/1999 |
| EP | 0928205 A1 | 7/1999 |
| EP | 0833704 B1 | 12/1999 |
| EP | 1016371 A1 | 7/2000 |
| EP | 0923949 A3 | 3/2001 |
| EP | 1110557 A2 | 6/2001 |
| EP | 1110558 A2 | 6/2001 |
| EP | 1140220 A1 | 10/2001 |
| EP | 1146915 A1 | 10/2001 |
| EP | 1257302 A1 | 11/2002 |
| EP | 0928205 B1 | 3/2003 |
| EP | 1110557 A3 | 4/2003 |
| EP | 1110558 A3 | 4/2003 |
| EP | 0907381 B1 | 9/2003 |
| EP | 0799621 B1 | 11/2003 |
| EP | 1380309 A1 | 1/2004 |
| EP | 0742017 B1 | 2/2004 |
| EP | 1016371 B1 | 2/2005 |
| EP | 1110558 B1 | 4/2005 |
| EP | 1552853 A2 | 7/2005 |
| EP | 1380309 B1 | 12/2005 |
| EP | 1647285 A1 | 4/2006 |
| EP | 1146915 B1 | 5/2006 |
| EP | 1140220 B1 | 9/2006 |
| EP | 1747027 A2 | 1/2007 |
| EP | 0923949 B1 | 2/2008 |
| EP | 1552853 A3 | 2/2008 |
| EP | 1908483 A2 | 4/2008 |
| EP | 1908483 A3 | 7/2008 |
| EP | 1110557 B1 | 3/2009 |
| EP | 1747027 A4 | 4/2009 |
| EP | 1146915 B2 | 9/2009 |
| EP | 2 138 127 A1 | 12/2009 |
| EP | 1 757 313 B1 | 3/2011 |
| EP | 1908483 B1 | 10/2012 |
| EP | 2572628 A1 | 3/2013 |
| EP | 2 614 840 A2 | 7/2013 |
| EP | 2572628 A4 | 7/2013 |
| EP | 1647285 B1 | 11/2013 |
| EP | 1747027 B1 | 1/2014 |
| EP | 2572628 B1 | 6/2014 |
| EP | 2786695 A1 | 10/2014 |
| ES | 2035189 T3 | 4/1993 |
| ES | 2059622 T3 | 11/1994 |
| ES | 2141472 T3 | 3/2000 |
| ES | 2206703 T3 | 5/2004 |
| ES | 2210455 T3 | 7/2004 |
| ES | 2213766 T3 | 9/2004 |
| ES | 2237894 T3 | 8/2005 |
| ES | 2238025 T3 | 8/2005 |
| ES | 2254864 T3 | 6/2006 |
| ES | 2263296 T3 | 12/2006 |
| ES | 2273518 T3 | 5/2007 |
| ES | 2300118 T3 | 6/2008 |
| ES | 2321580 T3 | 6/2009 |
| ES | 2263296 T5 | 12/2009 |
| ES | 2395962 T3 | 2/2013 |
| ES | 2447769 T3 | 3/2014 |
| ES | 2454549 T3 | 4/2014 |
| IE | 882341 L | 1/1989 |
| IE | 63435 B1 | 4/1995 |
| IN | 199802163 I2 | 3/2005 |
| IN | 225363 B | 9/2007 |
| IN | 200601331 P3 | 9/2007 |
| JP | S58-180130 A | 10/1983 |
| JP | S6449563 A | 2/1989 |
| JP | H05317390 A | 12/1993 |
| JP | H09609 A | 1/1997 |
| JP | H1028722 A | 2/1998 |
| JP | H11244362 A | 9/1999 |
| JP | H11253537 A | 9/1999 |
| JP | 2000-102508 A | 4/2000 |
| JP | 2000217892 A | 8/2000 |
| JP | 2001-204799 A | 7/2001 |
| JP | 2001309966 A | 11/2001 |

(56) References Cited

FOREIGN PATENT DOCUMENTS

| | | |
|---|---|---|
| JP | 2004-073259 A | 3/2004 |
| JP | 2004-167262 A | 6/2004 |
| JP | 2005-52410 A | 3/2005 |
| JP | 2005-205227 A | 8/2005 |
| JP | 2006-055325 A | 3/2006 |
| JP | 2006110349 A | 4/2006 |
| JP | 2006305379 A | 11/2006 |
| JP | 2007236965 A | 9/2007 |
| JP | 4153029 B2 | 9/2008 |
| JP | 4212743 B2 | 1/2009 |
| JP | 4303299 B2 | 7/2009 |
| JP | 4330664 B2 | 9/2009 |
| JP | 4459432 B2 | 4/2010 |
| JP | 4535293 B2 | 9/2010 |
| JP | 4722660 B2 | 7/2011 |
| JP | 2012-040240 A | 3/2012 |
| JP | 4892111 B1 | 3/2012 |
| JP | 4892116 B1 | 3/2012 |
| JP | 2012050817 A | 3/2012 |
| JP | 4948692 B2 | 6/2012 |
| KR | 20010062653 A | 7/2001 |
| KR | 100443600 B1 | 9/2004 |
| KR | 20060052161 A | 5/2006 |
| KR | 20070015215 A | 2/2007 |
| KR | 10-0702350 B1 | 4/2007 |
| KR | 101233733 B1 | 2/2013 |
| MX | 9702501 A | 4/1998 |
| MX | PA05010946 A | 4/2006 |
| NO | 311603 B1 | 12/2001 |
| NZ | 225382 A | 12/1996 |
| NZ | 236809 A | 12/1997 |
| NZ | 286537 A | 4/1998 |
| NZ | 521287 A | 8/2004 |
| RU | 2392970 C2 | 6/2010 |
| TW | 537906 B | 6/2003 |
| TW | I379695 B | 12/2012 |
| WO | 93/17726 A1 | 9/1993 |
| WO | 9641686 A1 | 12/1996 |
| WO | 9737692 A1 | 10/1997 |
| WO | 0038745 A1 | 7/2000 |
| WO | 0038746 A1 | 7/2000 |
| WO | 0158499 A1 | 8/2001 |
| WO | 02/41926 A1 | 5/2002 |
| WO | 02/43780 A1 | 6/2002 |
| WO | 2004/043499 A2 | 5/2004 |
| WO | 2005/011749 A2 | 2/2005 |
| WO | 2005118002 A2 | 12/2005 |
| WO | 2005118002 A3 | 8/2006 |
| WO | 2009058840 A1 | 5/2009 |
| WO | 2010/046891 A2 | 4/2010 |
| WO | 2011/041578 A2 | 4/2011 |
| WO | 2012/017720 A1 | 2/2012 |
| WO | 2012/037431 A1 | 3/2012 |
| WO | 2012/148589 A2 | 11/2012 |
| WO | 2012148589 A3 | 2/2013 |
| WO | 2016/010970 A1 | 1/2016 |
| WO | 2017/028980 A1 | 2/2017 |
| WO | 2017/043600 A1 | 3/2017 |
| WO | 2017/089258 A1 | 6/2017 |
| ZA | 9702844 B | 10/1998 |

OTHER PUBLICATIONS

PCT International Search Report (ISR) for International Application No. PCT/IB2019/055216 dated Oct. 31, 2019.

* cited by examiner

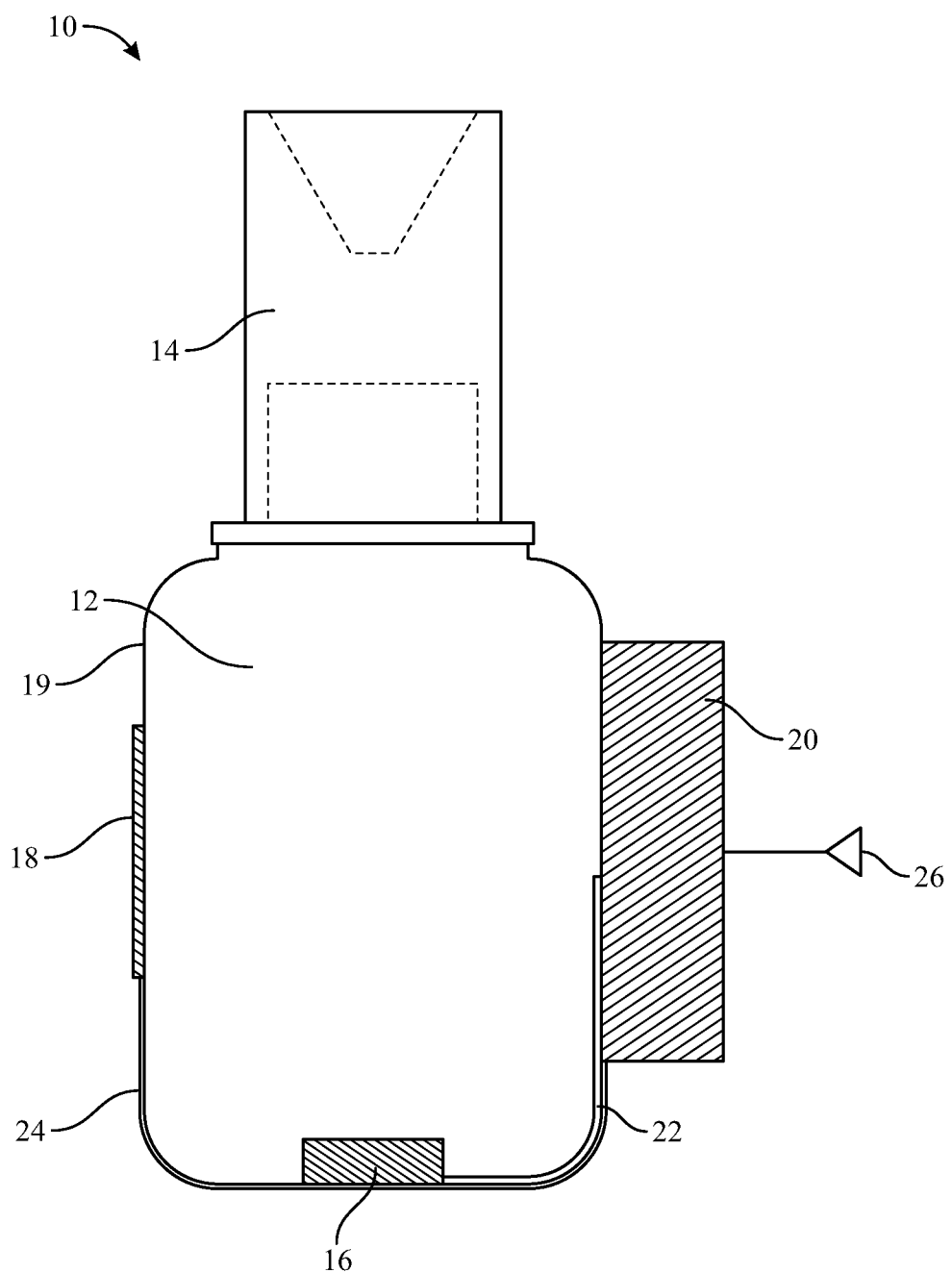

STERILIZATION-ASSISTANCE DEVICE

FIELD

The subject matter disclosed herein relates to sterilization-assistance devices including dry boosters, which are devices that assist in sterilizing medical devices having lumens, e.g., endoscopes.

BACKGROUND

Medical devices are typically sterilized before use in order to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO).

Certain sterilization techniques are conducted at pressures other than ambient pressure or atmospheric pressure. For example the STERRAD® System, STERRAD® NX System or STERRAD® 100NX System of Advanced Sterilization Products, Division of Ethicon US, LLC, a Johnson & Johnson company, are examples of sterilization systems, or sterilizers, that vaporize hydrogen peroxide and operate at low pressures, e.g., less than 200 millitorr.

Various elongate medical devices having lumens, e.g., endoscopes, are challenging to sterilize for various reasons. For example, because pressure within a lumen decreases from the lumen's inlet as a function of length and diameter, the pressure drop must be overcome to ensure that sterilant passes through the entire lumen and reaches all surfaces of the lumen. Further, lumens may collect debris or be blocked by fluids, such as rinse water.

A dry booster is a device that may be connected to a lumen of an elongate medical device. When subject to a sterilization process in which pressure changes are implemented, pressure differentials between the inside of a dry booster at one end of the lumen and a pressure chamber at the other end of a lumen help pass a sterilant through the lumen, which assists in sterilizing the lumen.

SUMMARY

A sterilization-assistance device is described herein. In some embodiments, the sterilization assistance device comprises a dry booster and at least one measurement device attached to the dry booster. In various embodiments, the at least one measurement device may include strain gauge. In various embodiments, the at least one measurement device may include a pressure sensor. In various embodiments, the at least one measurement device may include a pressure sensor and a strain gauge. The sterilization assistance device may also include a communication module. The communication module may be a wireless-communication module.

A sterilization-assistance device may be used according to the following exemplary steps. First, a sterilization-assistance device comprising a dry booster and a measurement device may be provided. In some versions of the method, the sterilization-assistance device may be provided with a measurement device including a strain gauge. In some versions of the method, the sterilization-assistance device may be provided with a communication module. This communication module may be a wireless-communication module.

Second, the sterilization-assistance device may be attached to an elongate medical device having a lumen. Third, the sterilization-assistance device and the elongate medical device may be placed into a vacuum chamber. Fourth, a first strain may be determined. Fifth, the first strain may be compared to a predetermined strain.

The method may additionally include determining whether the sterilization-assistance device is detached from the elongate medical device. The method may further include determining whether leaks occurred between the sterilization-assistance device and the elongate medical device. The method may further include determining whether a blockage occurred in the lumen. The method may further include aborting a sterilization process and reattaching the sterilization-assistance device to the elongate medical device.

A sterilization-assistance device may be used according to the following alternative exemplary steps. First, a sterilization-assistance device comprising a dry booster and a measurement device may be provided. In some versions of the method, the sterilization-assistance device may be provided with a measurement device including a pressure sensor. In some versions of the method, the sterilization-assistance device may be provided with a communication module. This communication module may be a wireless-communication module.

Second, the sterilization-assistance device may be attached to an elongate medical device having a lumen. Third, the sterilization-assistance device and the elongate medical device into a vacuum chamber. Fourth a first pressure within the dry booster may be determined. Fifth, a second pressure outside the dry booster may be determined. Sixth a first pressure difference between the first pressure and second pressure may be determined. Seventh the first pressure difference may be compared to a predetermined pressure difference.

The method may additionally include determining whether the sterilization-assistance device is detached from the elongate medical device. The method may further include determining whether leaks occurred between the sterilization-assistance device and the elongate medical device. The method may further include determining whether a blockage occurred in the lumen. The method may further include aborting a sterilization process and reattaching the sterilization-assistance device to the elongate medical device.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawing, in which like reference numerals identify the same elements and in which:

FIG. 1 depicts a schematic representation of a sterilization-assistance device.

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Dry boosters may be used to help draw chemical sterilants into a lumen of an elongate medical device, e.g., an endoscope. Dry boosters are disclosed in U.S. Pat. Nos. 6,451, 255 and 7,229,591, which are hereby incorporated by reference in their entirety. A dry booster may include an adapter to assist in establishing a connection between the dry booster and a lumen of an elongate medical device. An exemplary adapter is described in U.S. Pat. No. 6,187,265, which is hereby incorporated by reference in its entirety. Although dry boosters may be used to assist in sterilizing elongate medical devices having more than one lumen, the present disclosure focuses on elongate devices having a single lumen having a single inlet and a single outlet. Nonetheless, it should be apparent how to apply the teachings herein to elongate devices that may have more than a single lumen, a lumen having more than a single inlet, a lumen having more than a single outlet, or any combination thereof.

FIG. 1 shows a sterilization-assistance device 10, which includes a dry booster comprised of a vial 12 and an adapter 14 configured to connect vial 12 to an outlet of a lumen of an elongate medical device. Thus, sterilization-assistance device 10 may be connected to the elongated medical device before placing the elongate medical device into a vacuum chamber of a sterilizer, such as the STERRAD® System, STERRAD® NX System or STERRAD® 100NX System, and subjecting it to a sterilization procedure.

During many sterilization procedures involving a chemical sterilant, such as hydrogen peroxide, pressure within the sterilizer's vacuum chamber may be decreased or increased considerably and/or quickly. For example, the pressure in the vacuum chamber may be decreased from approximately 760 torr to approximately 2 torr over a time ranging between approximately 30 seconds to 15 minutes. For example, in the STERRAD® 100NX System, various phases of a sterilization cycle are performed during which pressure is lowered from approximately 760 torr to approximately 2 torr at differing rates based on the purpose of the phase. For example, some phases include injecting a sterilant, e.g., hydrogen peroxide (which slows down the rate of pressure change), whereas other phases are performed to remove residual moisture from within the chamber (which may cause evaporation that can also slow down the rate of pressure change), whereas other phases do not include injecting a sterilant or removing residual moisture (which may correspond to the fastest pressure change). The STERRAD® 100NX phase that has the slowest change in pressure may take from approximately 5 minutes to approximately 8 minutes to lower the pressure from approximately 760 torr to approximately 2 torr. The STERRAD® 100NX phase that has the fastest change in pressure takes approximately 1.5 minutes to change the pressure from approximately 760 torr to approximately 2 torr. Thus the average rate of negative change of pressure in the STERRAD® 100NX System's vacuum chamber may be between approximately 90 torr per minute and 510 torr per minute. Pressure changes over a portion of a cycle or instantaneous pressure changes, dP/dt, may be greater or less than the aforementioned average rates. Furthermore, the phases typically include an evacuation step during which the vacuum chamber is vented to the atmosphere and pressure within the vacuum chamber returns to atmospheric pressure. This pressure change may occur rapidly. For example, the pressure may be changed from approximately 150 mTorr to approximately 760 torr over a time ranging between approximately 10 seconds and one minute, such as thirty seconds. Thus the pressure can be changed at a positive rate of approximately 1500 torr per minute.

Because vial 12 and adapter 14 are in fluid communication with the vacuum chamber via the elongate device's lumen, the pressure within them may not be equal to the pressure within the vacuum chamber while the pressure therein is being changed. That is, the pressure within vial 12 and adapter 14 may "lag" behind the pressure in the vacuum chamber. Such pressure changes may cause surfaces of vial 12 to deflect inwardly or outwardly, which, in turn, could cause a leak between the vial and adapter or the adapter and the lumen. In some instances, this pressure changes may cause the dry booster to detach from the elongate medical device. Such a leak or detachment may prevent, or lower the ability of, the dry booster to pull sterilant through the lumen, which would reduce the effectiveness of the sterilization process and raise the likelihood that the sterilization process would not sterilize the entire lumen.

Should leaks or detachment occur, it may be advantageous to detect and address them when or promptly after they occur and before conducting the balance of a sterilization process that might be ineffective. For example, the sterilization process may be aborted and the elongate medical device removed from the vacuum chamber so that the dry booster may be reattached to the medical device or so that it may be replaced by another dry booster. Additionally, should a lumen of the elongate medical device be blocked, e.g., with residual water or cleaning solution left behind following a preparation for sterilization, it may be advantageous to detect and remove the blockage before conducting the balance of a sterilization process that might be ineffective.

The present disclosure is directed to sterilization-assistance devices, which comprise dry boosters and additional components that enable detection of leaks between the dry booster and an elongate medical device, detachment of the dry booster from the elongate medical device, and blockages in a lumen of the elongate medical device. For example, in some embodiments, a sterilization-assistance device 10 includes a dry booster comprising a vial 12 and an adapter 14, and at least one measurement device, such as a pressure sensor 16 and/or a strain gauge 18, and a communication module or relay 20.

In some embodiments a measurement device, such as pressure sensor 16, may be disposed upon or within vial 12, e.g., on an inner surface of vial 12. In some embodiments, pressure sensor 16 may be bonded to vial 12 with an epoxy. In other embodiments, vial 12 and pressure sensor 16 may be fabricated as a single unit by 3D printing techniques. Thus pressure within the vial 12 may be monitored as a function of time. When the booster is properly attached to an elongate medical device having a lumen and subject to a sterilization procedure, the pressure within vial 12 should differ from the pressure within the vacuum chamber but outside vial 12 due to a pressure drop through the lumen. This pressure drop is a function of the lumen's diameter and length in accordance with the Hagen-Poiseuille equation, although it should be understood that a theoretical pressure drop indicated by this equation may be somewhat different than an actual or experimental pressure drop. Nonetheless, an actual pressure drop should at least approximate the theoretical pressure drop. Accordingly, the difference in pressure between the inside and outside of a vial 12 that is attached to a clean (i.e., unblocked) lumen and that does not experience leaks or detachment may be determined—or predetermined—such that this difference may be used as a reference during subsequent sterilization procedures. For example, a sterilization-system manufacturer or sterilization-assistance device manufacturer may predetermine a first reference pressure difference between the inside and outside of vial 12 and corresponding to the scenario where no leaks occur between vial 12 and adapter 14, between adapter 14 and the elongate medical device, and where the dry booster remained fully attached to the elongate medical device. Similarly, the manufacturer may predetermine a second reference pressure difference between the inside and the outside of vial 12 and corresponding to the scenario where leakage occurs. Further, the manufacturer may predetermine a third reference pressure difference between the inside and outside of vial 12 and corresponding to the scenario where the dry booster detaches from elongate medical device. This third reference pressure difference may be approximately zero or close to zero because when the dry booster is detached from the elongate medical device, gas need not pass through the device's lumen to affect the pressure within vial 12. Accordingly, pressure inside and outside the dry booster should be substantially similar. Additionally, the manufacturer may predetermine a fourth reference pressure difference corresponding to the scenario where the lumen in the elongate medical device is blocked.

A healthcare provider who uses a sterilizer to sterilize an elongate medical device may monitor pressure differences between a sterilization-assistance device attached to the elongate medical device and a vacuum chamber of the sterilizer. The healthcare provider may compare the monitored pressure difference to the predetermined reference pressure difference to determine whether the monitored pressure corresponds to a scenario of no leaking, leaking, detachment between the sterilization-assistance device and the elongate medical device, or lumen blockage. Alternatively, the pressure monitoring may automated and may be performed by the sterilizer or a stand-alone monitoring system, explained below. Thus, when a problem such as leakage, detachment, or blockage is detected, the sterilization process may be aborted to allow a healthcare provider to remedy the problem, e.g., by reattaching the dry booster, attaching a new dry booster, and/or removing the blockage.

In some embodiments, sterilization assistance device 10 may additionally or alternatively include another measurement device, e.g., strain gage 18, disposed upon or within vial 12, e.g., on an outer surface 19 of vial 12. In some embodiments, strain gage 18 may be bonded to vial 12 with an epoxy. In other embodiments, vial 12 and strain gage 18 may be fabricated as a single unit by 3D printing techniques.

Assuming that sterilization assistance device 10 is properly connected to an elongate medical device and that no leaks occur during a sterilization process, the difference in pressures inside and outside vial 12 may cause vial 12 to deform, causing strain in vial 12. This strain may be measured by strain gage 18. Accordingly, similar to the predetermined reference pressure information described above, predetermined reference strain information may be collected. A sterilization-system manufacturer or sterilization-assistance device manufacturer may predetermine a first reference strain profile corresponding to the scenario where no leaks occur between vial 12 and adapter 14, between adapter 14 and the elongate medical device, and where the dry booster remains fully attached to the elongate medical device. The manufacturer may also predetermine a second reference strain profile corresponding to the scenario where leakage occurs. Further, the manufacturer may predetermine a third reference strain profile corresponding to the scenario where the dry booster detaches from elongate medical device. This third reference strain profile may be approximately zero and constant because when the dry booster is detached from the elongate medical device, gas need not pass through the device's lumen to affect the pressure within vial 12 such that deformation of vial 12 should not occur. Additionally, the manufacturer may predetermine a fourth reference strain profile corresponding to the scenario where the lumen in the elongate medical device is blocked.

A healthcare provider conducting device sterilization may monitor strain of a sterilization-assistance device attached to an elongate medical device, and compare the monitored strain to the predetermined reference strain profiles to determine whether the monitored strain corresponds to a scenario of no leaking, leaking, detachment between the sterilization-assistance device and the elongate medical device, or lumen blockage. Alternatively, the pressure monitoring may be performed by the sterilizer or a stand-alone monitoring system, explained below. Thus, when a problem such as leakage, detachment, or blockage is detected, the sterilization process may be aborted to allow a healthcare provider to remedy the problem, e.g., by reattaching the dry booster, attaching a new dry booster and/or removing the blockage.

Pressure sensor 16 and/or strain gauge 18 may communicate with a communication module or relay 20. A connection, such as by wires 22 and 24, may be established from sensor 16 and/or gauge 18 to communication module 20 to allow communication between these components. Communication module 20 may be attached directly to a surface, e.g., surface 19 of the sterilization-assistance device, e.g., with epoxy, or in some embodiments, it may not be attached to sterilization-assistance device, instead only connected thereto by wires 22 and/or 24.

In turn communication module 20 may communicate by wire or wirelessly with a data collection and processing system ("DCPS"). Communication module 20 relays any information it receives from pressure sensor 16 and/or strain gauge 18 to the DCPS for processing. The DCPS may perform the comparisons of pressure and strain data necessary to determine whether there are leaks between a dry booster and an elongate medical device, whether the dry booster is detached from the elongate medical device, or whether there is a blockage in a lumen of the elongate medical device. The DCPS may be a control system of the sterilizer or a stand alone device that is located outside the sterilizer and may be entirely separate from the sterilizer. The DCPS may include a processor, a nontransitory storage medium, a receiver, a screen, and, optionally, an alarm. In those embodiments where the connection between module 20 and the DCPS is a wired connection, the receiver may include a standard wire connector, e.g., a pin connector or coaxial cable connector. In those embodiments where the connection between module 20 and the DCPS is a wireless connection, the receiver may include an antenna 26 and any other components necessary to establish wireless communication and successfully transfer data from module 20 and to the DCPS. Similarly, in these wireless embodiments, module 20 must also include components necessary to establish wireless communication and successfully transfer data from module 20 to the DCPS. For example, the wireless communication may be performed according to the Bluetooth® wireless technology standard.

In some embodiments, the DCPS may be the control system of the sterilizer. In other embodiments, the DCPS may be a stand-alone device, separate from the sterilizer, such as a stand alone user interface device. In some embodiments, the stand-alone device may be a portable computer, such as a Smartphone containing an application capable of interfacing with communication module 20 using, e.g., wireless communication capabilities of the Smartphone. The predetermined reference pressure differences and/or predetermined reference strain profiles may be stored in the non-transitory storage medium of the DCPS. Upon receiving data from the pressure sensor and/or the strain gauge, as relayed by communication module 20, the processor of the DCPS may compare the data to the reference information and determine whether leaks occurred, detachment occurred, or blockage occurred. The DCPS may notify healthcare personnel of the determination by providing a message on its display and/or sounding an alarm. In those embodiments where the DCPS is the control system of the sterilizer, the DCPS may automatically abort a sterilization procedure upon determining leakage, detachment, or blockage. In those embodiments where the DCPS is included in a stand-alone device, e.g., a stand-alone user interface device, the DCPS would alert healthcare personnel of the leakage, detachment, or blockage and the healthcare personnel could manually abort the sterilization procedure.

Because communication module 20 is a component of sterilization assistance device 10, it will be subject to sterilization procedures. Thus communication module 20 should be configured to function, i.e., relay data from pressure sensor 16 and/or strain gauge 18 to the DCPS, while being exposed to sterilant, low temperatures, and low pressures. U.S. Patent Application Publication No. US2009/0225517, which is hereby by reference in its entirety, describes a system suitable for use as communication module 20. This reference describes using a container to protect a wireless transmitter that operates within an autoclave.

Predetermined reference pressure differences and predetermined reference strain profiles may also be correlated with volume flow rates of sterilants such that a volume flow rate of a sterilant through a lumen of an elongate medical device and into a dry booster may be determined. Efficacy of a sterilization process upon an elongate medical device having a lumen depends upon delivery a sufficient amount of sterilant through the lumen. Accordingly, a volume flow rate of a sterilant through a lumen, determined during an active sterilization process, may be used to adjust, i.e., shorten or lengthen, the amount of time that the sterilant should be exposed to the lumen at that volume flow rate. Such an adjustment helps ensure that a correct amount of sterilant passes through the lumen of the elongate medical device, and in some instances may save time and avoid wasting sterilant. The adjustment may be performed by a processor within the sterilizer's control system, which may then make adjustments to the sterilization procedure.

Sterilization-assistance device 10 may be used to perform the following example methods. First, a dry booster of a sterilization-assistance device 10 may be connected to an elongate medical device having a lumen, e.g., an endoscope. Second, sterilization-assistance device, along with the elongate medical device, may be placed into a vacuum chamber of a sterilizer. Third, a sterilization process that includes changing a pressure within the vacuum chamber may be commenced. Fourth, in those embodiments that include a pressure sensor 16, pressure sensor 16 may measure the pressure within a vial 12 of sterilization-assistance device. Fifth, in those embodiments that include a strain gauge 18, strain gauge 18 may measure strain upon a surface of vial 12. Sixth, communication module 20 may receive pressure data generated by pressure sensor 16 and/or strain data generated by strain gauge 18. Seventh, communication module 20 may relay the pressure and/or strain data to a DCPS, which may be a control system of the sterilization or may be included in a stand alone device, such as a stand alone user-interface device. Eighth, a processor of the DCPS may compare the pressure and/or strain data to predetermined reference data. Ninth, the processor of the DCPS may determine whether a connection between a dry booster of sterilization-assistance device and the elongate medical device leaked, whether the dry booster became detached from the elongate medical device, and/or whether there are any blockages within the lumen of the elongate medical device. Tenth, a user-interface, such as a display or an alert, may notify healthcare personnel of the DCPS's determination concerning leakage, detachment, and blockage. Eleventh, the sterilization process may be ended. The sterilization process may be ended or aborted before it has completed when leakage, detachment, or blockage is determined by the DCPS. Twelfth, healthcare personnel may reattach the dry booster of the sterilization-assistance device 10, may attach a new or different dry booster of another sterilization-assistance device 10, or may remove a blockage within the lumen.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of using a sterilization-assistance device, comprising:
   providing the sterilization-assistance device, the sterilization-assistance device comprising a dry booster and a measurement device including a strain gauge attached to the dry booster;
   attaching the sterilization-assistance device to an elongate medical device having a lumen;
   placing the sterilization-assistance device attached to the elongate medical device into a vacuum chamber;
   determining a first strain; and
   comparing the first strain to a predetermined strain.

2. The method of claim 1, further comprising determining whether the sterilization-assistance device is detached from the elongate medical device.

3. The method of claim 2, further comprising determining whether leaks occurred between the sterilization-assistance device and the elongate medical device.

4. The method of claim 3, further comprising determining whether a blockage occurred in the lumen.

5. The method of claim 4, further comprising:
   aborting a sterilization process; and
   reattaching the sterilization-assistance device to the elongate medical device.

6. The method of claim 5, wherein the sterilization-assistance device further comprises a communication module.

7. The method of claim 6, wherein the communication module is a wireless-communication module.

8. A method of using a sterilization-assistance device, comprising:
   providing the sterilization-assistance device, the sterilization-assistance device comprising a dry booster and a measurement device including a pressure sensor disposed within the dry booster;
attaching the sterilization-assistance device to an elongate medical device having a lumen;
placing the sterilization-assistance device attached to the elongate medical device into a vacuum chamber;
determining a first pressure within the dry booster;
determining a second pressure outside the dry booster;
determining a first pressure difference between the first pressure and second pressure; and
comparing the first pressure difference to a predetermined pressure difference.

9. The method of claim 8, further comprising determining whether the sterilization-assistance device is detached from the elongate medical device.

10. The method of claim 9, further comprising determining whether leaks occurred between the sterilization-assistance device and the elongate medical device.

11. The method of claim 10, further comprising determining whether a blockage occurred in the lumen.

12. The method of claim 11, further comprising:
aborting a sterilization process; and
reattaching the sterilization-assistance device to the elongate medical device.

13. The method of claim 12, wherein the sterilization-assistance device further comprises a communication module.

14. The method of claim 13, wherein the communication module is a wireless-communication module.

* * * * *